(12) United States Patent
Louie et al.

(10) Patent No.: US 7,496,521 B1
(45) Date of Patent: Feb. 24, 2009

(54) PRESCRIPTION ORDER IDENTIFICATION SYSTEM

(75) Inventors: Shelton Louie, Vancouver, WA (US); Stephen A. Garrett, Vancouver, WA (US); Mark B. Smith, Vancouver, WA (US)

(73) Assignee: GSL Solutions, Inc., Vancouver, WA (US)

( * ) Notice: Subject to any disclaimer, the term of this patent is extended or adjusted under 35 U.S.C. 154(b) by 805 days.

(21) Appl. No.: 09/991,529

(22) Filed: Nov. 16, 2001

Related U.S. Application Data

(63) Continuation-in-part of application No. 09/715,439, filed on Nov. 16, 2000.

(51) Int. Cl.
*G06Q 10/00* (2006.01)
(52) U.S. Cl. .......................................... 705/2; 705/22
(58) Field of Classification Search ................ 705/2, 705/22
See application file for complete search history.

(56) References Cited

U.S. PATENT DOCUMENTS

| | | | | |
|---|---|---|---|---|
| 5,646,592 | A * | 7/1997 | Tuttle | 340/545.6 |
| 5,689,238 | A * | 11/1997 | Cannon et al. | 340/572.1 |
| 5,771,657 | A * | 6/1998 | Lasher et al. | 53/55 |
| 5,907,493 | A * | 5/1999 | Boyer et al. | 700/231 |
| 6,150,942 | A * | 11/2000 | O'Brien | 340/573.1 |
| 6,259,654 | B1 * | 7/2001 | de la Huerga | 368/10 |
| 6,415,295 | B1 * | 7/2002 | Feinberg | 707/104.1 |
| 6,502,005 | B1 * | 12/2002 | Wrubel et al. | 700/116 |
| 6,529,786 | B1 * | 3/2003 | Sim | 700/90 |
| 2001/0017817 | A1 * | 8/2001 | De La Huerga | 368/10 |
| 2001/0040512 | A1 * | 11/2001 | Hines et al. | 340/825.49 |
| 2002/0180588 | A1 * | 12/2002 | Erickson et al. | 340/10.2 |
| 2003/0086338 | A1 * | 5/2003 | Sastry et al. | 368/10 |
| 2003/0200726 | A1 * | 10/2003 | Rast | 53/443 |
| 2004/0036623 | A1 * | 2/2004 | Chung | 340/825.49 |

* cited by examiner

*Primary Examiner*—Elaine Gort
(74) *Attorney, Agent, or Firm*—Ipsolon llp (57) ABSTRACT

A pharmacy prescription order identification system that has a uniquely identified tag that travels with the prescription order throughout the pharmacy and is wirelessly connected to a computer system. The tag includes one or more worker signaling devices, such as lights or an audio speaker, that activate in response to either input from the pharmacy worker or other predetermined criteria to identify the prescription order to the pharmacy worker. In a preferred embodiment, the tag includes a plurality of worker signaling devices, and the activation of each transducer alerts a pharmacy worker to a different status of the prescription order. More preferably, the prescription order identification system includes a computer system that allows a pharmacy worker to individually access a customer's record, then activate the worker singling devices on the tag associated with that customer's prescription order, thereby allowing a particular prescription order within the pharmacy to be easily identified. In addition, the computer system can automatically monitor the status of all pending prescription orders within the pharmacy and using predefined criteria, such as the elapsed time the prescription order has been within the pharmacy, automatically activate the worker signaling devices on the tags associated with particular prescription orders meeting that criteria.

17 Claims, 6 Drawing Sheets

PRESCRIPTION ORDER IDENTIFICATION SYSTEM

This application is a continuation in part of U.S. patent application Ser. No. 09/715,439, filed on Nov. 16, 2000, now pending,

FIELD OF THE INVENTION

The present invention relates to a system for identifying prescription orders in a pharmacy. In particular, a tag that travels with the prescription order and is wirelessly connected to a computer system identifies itself to a pharmacy worker in response to either input from the pharmacy worker or other predetermined criteria.

BACKGROUND OF THE INVENTION

A typical local retail pharmacy fills thousands of prescription orders per week. Moreover, as the general population ages and new beneficial drugs are introduced, prescription order volumes to be filled at retail pharmacies are expected to double within the next few years. This present and expected increase in order volume places enormous pressure on pharmacists and other pharmacy workers, who strive to fill each order efficiently, accurately and quickly.

Most customers have a limited view of how a typical retail pharmacy works. They often think that when they present a written prescription order to a local retail pharmacy, such as at their corner drugstore, a pharmacist will personally greet them, review their order, complete and file the necessary paperwork required by applicable laws, fill the prescription order, and present the filled order to the customer, all within a few minutes. However, in addition to increasing volume, the traditional retail pharmacist is now faced with a large variety of additional tasks, including obtaining proper insurance payment authorization, and in some cases verifying the refillabilty of a particular prescription order. Moreover, orders may now enter the pharmacy through a wide variety of mediums, such as via facsimile, phone call, and e-mail.

In light of the increasing demands and obligations placed on retail pharmacies, they are evolving into more efficient organizations having numerous employees performing individual tasks associated with filling each prescription order. For example, when a customer presents a prescription to the pharmacy, a clerk may take the prescription order and enter it into a computer system that verifies insurance information. If approved, he or she may then prepare a prescription label to be placed on the package that will ultimately contain the prescribed drug. The clerk may then present the prescription order and label to a technician, usually stationed at another location within the pharmacy, who will physically fill the prescription by placing the appropriate quantity of the prescribed drug within the bottle and attach the label. Pursuant to applicable laws, a registered pharmacist then reviews the technician's work, and approves the dispersal of the completed prescription order to the customer. A clerk may then place the filled prescription in a storage area to await customer pick-up. Upon customer pick-up, the clerk files the written prescription order and any other appropriate paperwork related to the transaction, such as signed insurance forms and any informed consent paperwork. This type of system allows the pharmacy to quickly, efficiently, and economically fill numerous prescription orders.

Given the high volume of prescription orders being filled, the large number of people performing individual tasks associated with filling each prescription order, and the numerous locations within the pharmacy that a prescription order can be positioned as it is being filled, it is important that the prescription order, and ultimately the filled prescription, be easily located throughout the process. For example, if a particular prescription order is denied payment by insurance, a clerk may hold the prescription order aside while the customer is contacted. If the customer presents himself to another clerk at the pick-up window, while the first clerk is attempting to call the customer at home, the second clerk often has no way of knowing the current status of the prescription order, or where it is in the order filling process. Accordingly, the second clerk is forced to search each location within the pharmacy.

In addition, should a prescription order be inadvertently misplaced within the pharmacy, it is often difficult to find, thereby needlessly delaying the filling process and wasting worker time to locate it. Similarly, it is desirable for pharmacy workers to be able to easily identify and locate particular prescription orders that meet predefined criteria, such as having fallen behind a promised customer pick-up time.

Some pharmacy vendors have attempted to overcome these problems by offering systems that manually track prescription orders within a pharmacy. In particular, they require the worker at a given station to manually enter into a computer the fact that they have received a particular prescription order at that particular location. However, in addition to the lost time associated with manually entering this information at each station, evidence suggest that many workers find this repetitive task cumbersome, and as a result, they often fail to manually enter such information. Accordingly, these types of tracking systems are rendered useless.

Similarly, some pharmacy vendors have attempted to automate the prescription filling aspect of a pharmacy by incorporating an automatic assembly line process for filling prescription orders. In particular, an operator enters a prescription order into a computer system, which causes a conveyor-type system to deliver an empty vial to an automated drug dispenser. The filled vial is then automatically matched with a label and presented to a pharmacist for final review and approval. While these types of devices facilitate the quick and efficient filling of prescription orders, they are expensive for use in a retail pharmacy environment, and they occupy a large amount of limited space within the pharmacy. Moreover, they still require pharmacy workers to perform manual tasks such as verifying insurance and renewability of the prescription, and processing the various forms of prescription orders before and after they are entered into the automated system. Accordingly, they do not permit the easy location of prescription orders as they travel within the automated pharmacy environment, or easy identification of the prescription orders that have fallen behind a predetermined timeframe established for the pharmacy to fill the prescription order.

SUMMARY OF THE INVENTION

Despite the known pharmacy prescription order identification and tracking systems, there remains a need for a pharmacy prescription order identification system that allows a pharmacy worker to easily identify and distinguish a particular prescription order from a plurality of prescription orders within the pharmacy. Similarly, there remains a need for a pharmacy prescription order identification system that automatically monitors the status of all prescription orders within the pharmacy and identifies only those orders that satisfy a predetermined criteria. In addition to other benefits that will become apparent in the following disclosure, the present invention fulfills these needs.

The present invention is a pharmacy prescription order identification system that includes a uniquely identified tag that travels with the prescription order throughout the pharmacy and is wirelessly connected to a computer system. The tag includes one or more worker signaling devices, such as lights or an audio speaker, that activate in response to either input from the pharmacy worker or other predetermined criteria to identify the prescription order to the pharmacy worker.

In a preferred embodiment, the tag includes a circuit having a receiver, power source, plurality of transducers, such as lights and/or an audio speaker, processor and related memory operably engaging each other to activate the transducer upon a commanded signal received from a transmitter operably secured to a computer system. The memory on the tag includes a unique identifier, which is also known by the computer system, such that the signal from the computer system only activates the transducers on that tag from a plurality of tags within the pharmacy.

In an alternative preferred embodiment, the pharmacy prescription order identification system also serves as a tracking and monitoring system. The tag is preferably a transceiver with a transducer operably secured thereto, such as a conventional Radio-Frequency Identification ("RFID") tag with one or more lights or speakers connected thereto. The computer system includes a plurality of transceivers, one spaced at each key locations throughout the pharmacy to detect the presence of each tag positioned near a particular transceiver of the computer system. The detected locations are compiled via the computer system and associated with the customer, such that at any given time, the location of the prescription order within the retail pharmacy can be quickly and easily determined.

The computer system includes appropriate applications that allow a pharmacy worker to individually locate a particular customer's record in a database, then activate the worker singling devices on each tag associated with that customer's prescription order, thereby allowing that particular customer's prescription order within the pharmacy to be easily identified. In addition, the computer system can monitor the status of a particular order, such as the time it has been in the pharmacy, or even a particular area within the pharmacy, and automatically activate the worker signaling devices on tags that satisfy a particular criteria, such as having exceeded a predetermined time criteria, thereby alerting the pharmacy workers to prioritize the filling these prescription orders.

Additional objects and advantages of the present invention will be apparent from the detailed description of the preferred embodiment thereof, which proceeds with reference to the accompanying drawings.

DETAILED DESCRIPTION OF PREFERRED EMBODIMENTS

An economical and easy to use pharmacy prescription order identification system 10 that includes a uniquely identified identification tag 16 with one or more worker signaling devices, which are also known as transducers 17 thereon, such as lights 17a (FIG. 2) or an audio speaker 17b (FIG. 2), that travels with the prescription order 12 throughout the pharmacy 14 and is wirelessly connected to a computer system 20 is disclosed in FIGS. 1-7. The transducers 17 activate in response to either computer input from the pharmacy worker or other predetermined criteria to identify the prescription order 12 to the pharmacy worker.

A. Tag with Worker Signaling Devices

Figure 1:
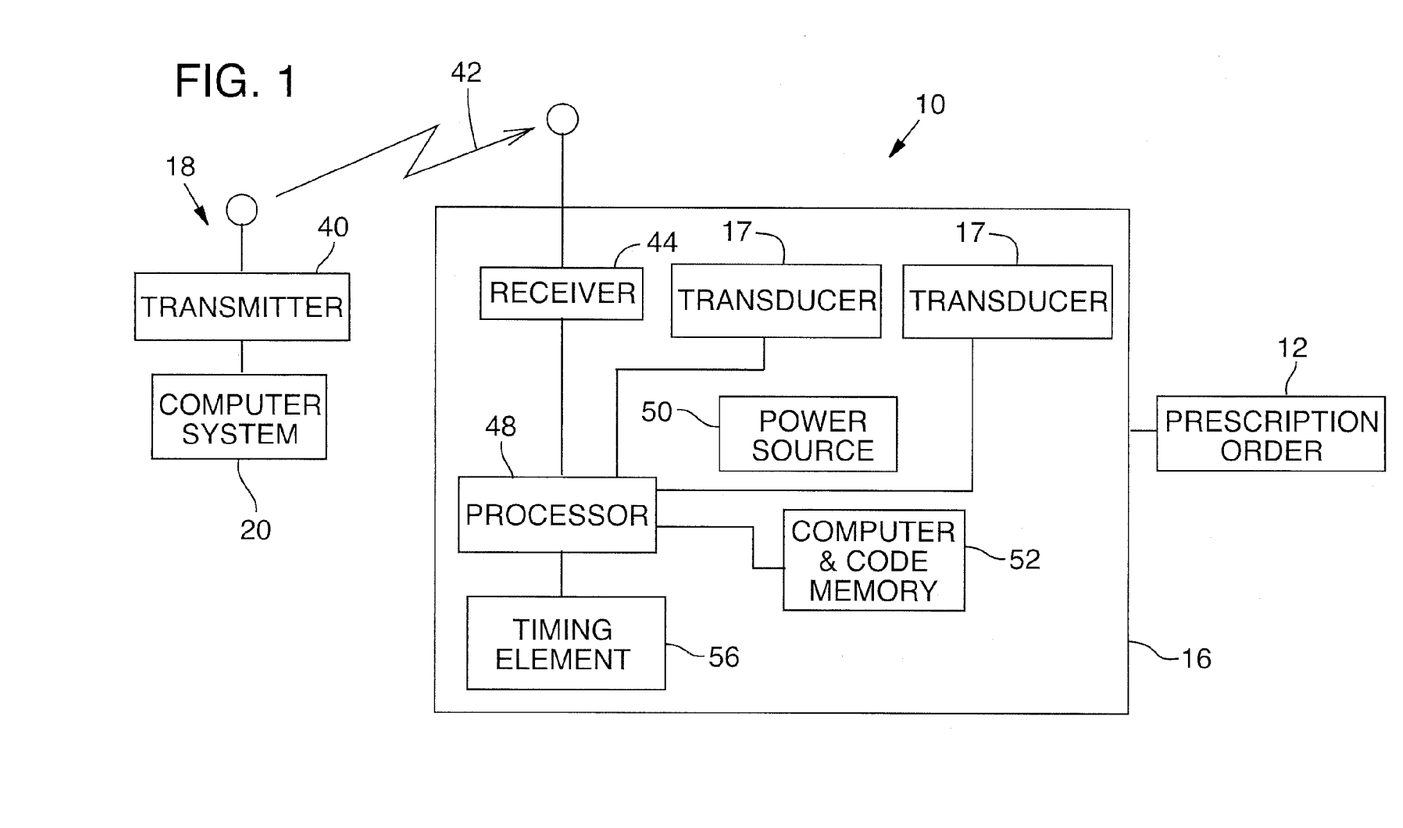
FIG. 1 is a schematic diagram of an identification tag and an associated transmitter operably secured to a computer system in accordance with an embodiment of the present invention.
Figure 4:
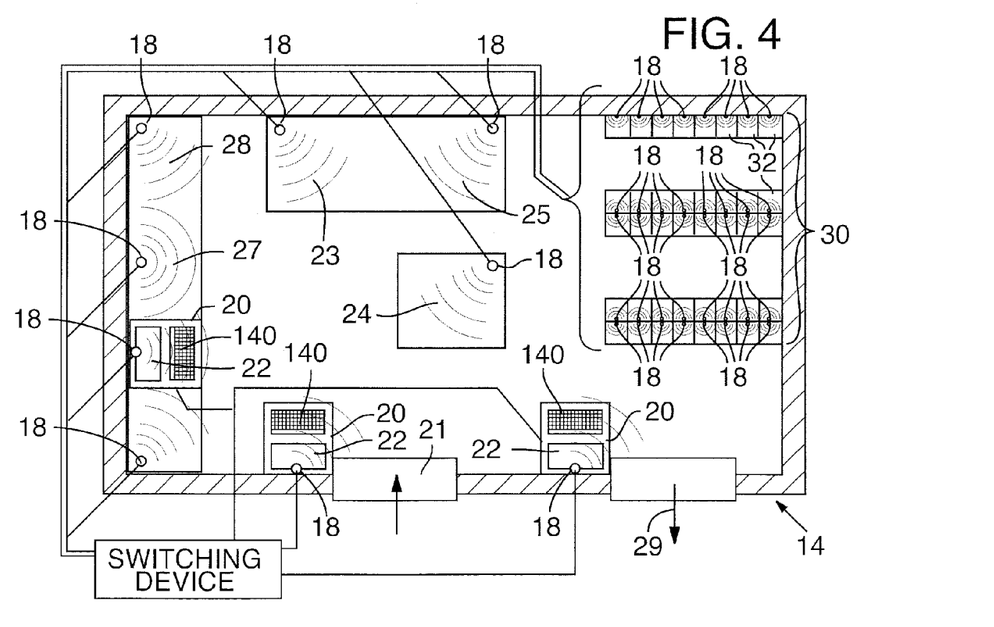
FIG. 4 is a schematic view of a prescription order tracking system in accordance with an embodiment of the present invention.

FIG. 1 discloses an exemplar tag 16 and related components for locating a prescription order 12 in a pharmacy 14 (FIG. 4). The computer system 20 is operably connected to a transmitter 40 that transmits a signal 42 to a plurality of tags 16. Each tag 16 is assigned to travel with a unique prescription order 12, and includes a receiver 44 for receiving the signal and internal circuitry such as a processor 48, power source 50 and memory 52 which contains a unique identifier for that tag and control logic to activate one or more transducers 17, which serve as the worker signaling devices, upon the tag 16 receiving a unique signal 42 from the transmitter 40.

Figure 2:
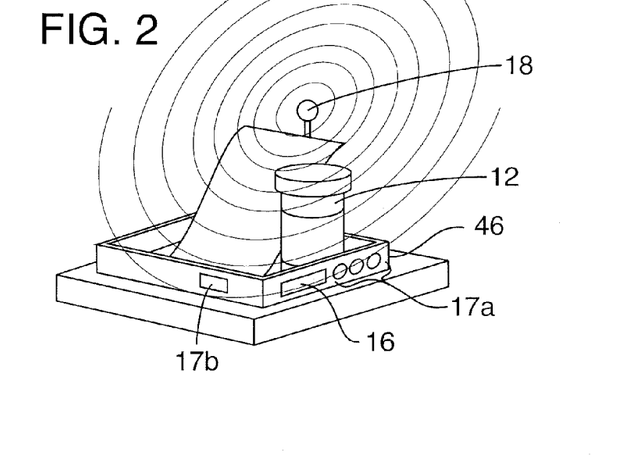
FIG. 2. is an isometric view of showing a possible orientation of the identification tag of FIG. 1 in relation to a customer prescription order.

Preferably, the transducer 17 is either a light 17a (FIG. 2) or audio speaker 17b (FIG. 2). More preferably, there are a plurality of transducers 17 that can be individually activated on each tag 16. For example, there can be three lights of different colors (i.e. red, yellow, and green), which can be activated either alone or in combination to identify the status of that prescription order 12. With a different status being denoted by a different transducer being activated.

The tag 16 can include an internal timing element 56 that activates one or more transducers 17 in sequence based on a predetermined timing interval. For example, the tag 16 can be programmed to light a green light or not light any light, thereby denoting the prescription order is on schedule, when a predetermined timing event has not occurred, light a yellow light when the predetermined timing event is close to approaching, and light a red light when the predetermined timing event has been exceeded.

The computer system 20 includes appropriate application programs 136 (FIG. 6) and memory 122 (FIG. 6) to correlate a customer's identifying information such as their name, phone number, and the like, with the unique identifier on the tag traveling with that prescription order. Accordingly, when a pharmacy worker wishes to locate a customer's prescription order, her or she may find the customer's identifying information on the computer system 20, and cause the computer system to transmit the unique signal 42 through the transmitter 40 to wirelessly activate one or more transducers 17 on the tag 16 associated with the customer's prescription order 12. For example, the tag's audio speaker 17b (FIG. 2) may make an audible sound, or one or more lights 17a (FIG. 2) on the tag 16 may light and/or blink.

Figure 3:
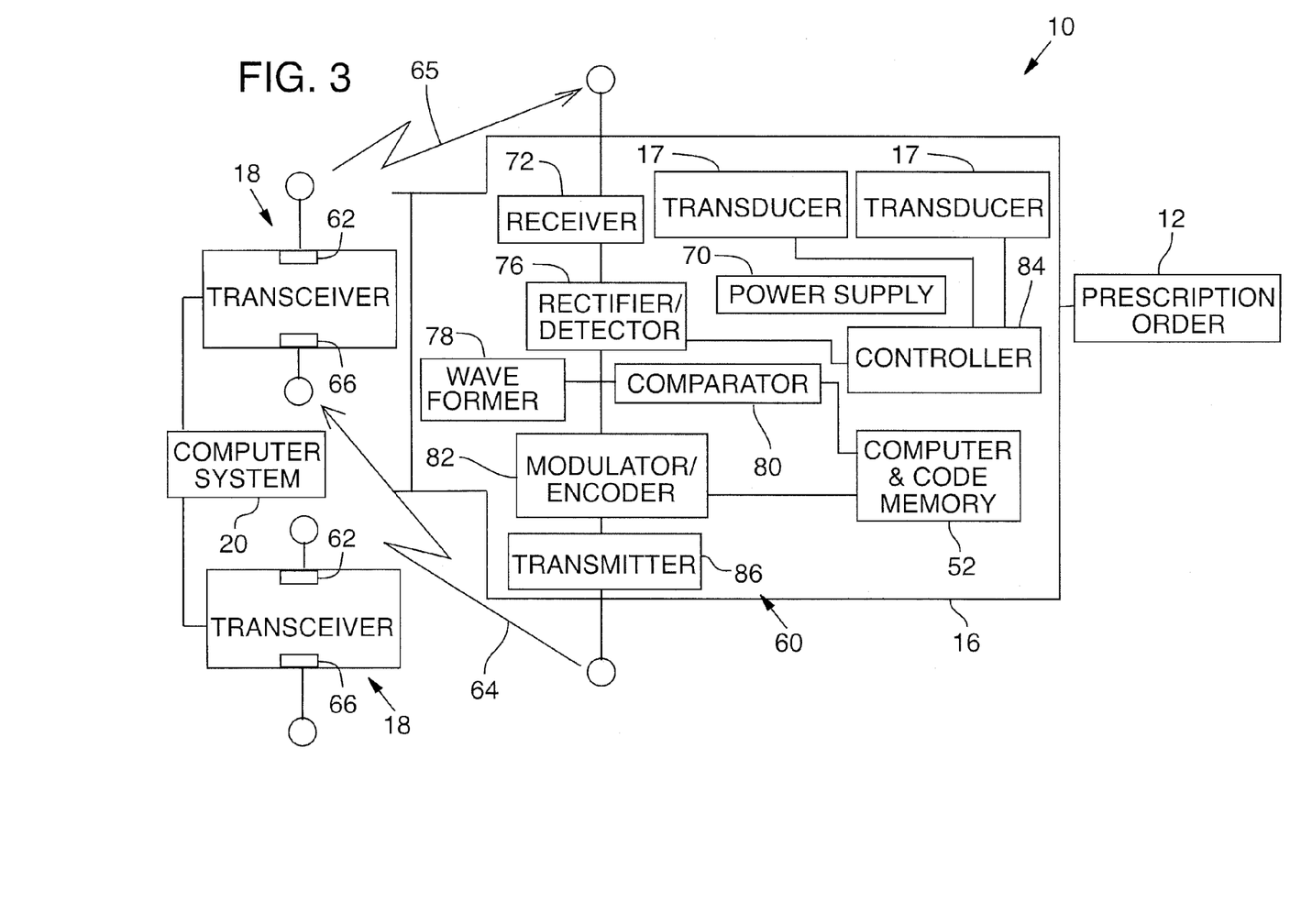
FIG. 3 is a schematic diagram of an active transponding tag and an associated transponder operably secured to a computer system in accordance with an alternative preferred embodiment of the present invention.

Alternatively, and as shown in FIG. 3, the tag 16 may be a transceiver 60 with at least one transducer 17 operably secured thereto, such as for example, a conventional Radio-Frequency Identification ("RFID") tag with one or more lights 17a (FIG. 2) or audio speakers 17b (FIG. 2) connected thereto. Each tag 16 can be either passive or active. In the passive mode, the tag circuitry accumulates and then returns a signal, if the interrogation signal matches a predefined code sequence stored in memory in the tag's circuitry. In an active mode, each tag further includes a power supply 70 that assists with signal amplification, detection and/or wave forming. As shown in FIG. 3, each tag transponder can include a receiver 72, a power supply 70, a rectifier/detector 76, a wave former 78, a comparator 80 with associated memory 52, a modulator/encoder 82, a controller 84, the one or more transducers 17, and a transmitter 86.

Preferably, a plurality of fixed or handheld transceivers, which are collectively referred to as tag readers 18 herein, are spaced apart from each other and positioned at desired locations within the pharmacy 14 (FIG. 4) to define spaced-apart interrogation zones within the pharmacy. As shown in FIG. 3, each tag reader 18 includes a front-end transmitter 62 that generates a digitally encoded signal 65. Preferably, the signal 64 is chosen to facilitate a response from only one uniquely coded tag 16. The receiver portion 66 of the tag reader 18 can induce a coded signal detector that senses the transponder signal 64 and correlates it with a stored code to identify that the tag 16 is present in a particular interrogation zone, thereby also determining the tag's location within the pharmacy.

The computer system 20 can also use conventional triangulation techniques to determine the location of the tag within the pharmacy. In which case, only two spaced-apart tag readers 18 need be placed within the pharmacy. Alternatively, using quasi-sonar-type locating techniques, a single tag reader 18 could be used determine the location of the tag within the pharmacy.

Each tag 16 can be either passive or active. In the passive mode, the tag circuitry accumulates and then returns a signal, if the interrogation signal matches a predefined code sequence stored in memory in the tag's circuitry. In an active mode, each tag's power supply 70 powers the system to assist with signal amplification, detection and/or wave forming.

During use, an interrogation signal 65 is received by the receiver 72 and decoded by the rectifier/detector 76. The rectifier/detector 76 generates a waveform which can be returned to the interrogating tag reader 18 via transmitter 86, if the encoded interrogation signal correlates with a sequence stored in memory 52. The controller 84 activates one or more transducers in response to a detected command signal 65.

Preferably, the one or more transducers 17 are either a light 17a (FIG. 2) or audio speaker 17b (FIG. 2). More preferably, there are a plurality of transducers 17 that can be individually activated on each tag. For example, there can be three lights of different colors (i.e. red, yellow, and green), which can be activated either alone or in combination to identify the status of that prescription order. With a different status being denoted by a different transducer being activated.

B. Prescription Order Tracking Through Pharmacy

Tags 16 with transducers 17 may also be used to track the location of the prescription order as it travels throughout the pharmacy 14. For example and referring to FIG. 4, a prescription order 12 is presented to the pharmacy 14 and assigned an identification tag 16 with one or more transducers 17 thereon. Tag readers 18 are positioned at key locations throughout the pharmacy 14 and in communication with the computer system 20 having a display 22, such that the movement of the prescription order 12 throughout the pharmacy 14 automatically detects and records the location of the tag 16 without further worker input. Accordingly, a worker can easily determine the location of the prescription order 12 within the pharmacy by entering commands in the computer system 20 with a user input device such as a keyboard 120 to display the location of the prescription order 12 on the computer display 22.

Each tag reader 18 is placed in communication with the computer system such that information regarding the customer, his prescription order position, and the status of his order can be readily displayed on the computer display 22, and thereby facilitate location of the prescription order 10 within the pharmacy 14.

Preferably, the identification tags 16 are attached to the prescription label, detachably secured to the prescription order, or rigidly secured to a carrier 46 (FIG. 2) containing these documents and other materials related to filling the prescription. The tags themselves can be either rigidly or detachably secured to the prescription order. For example, the tags can be directly secured to the prescription with adhesive or secured within a prescription lid. Also, the tags can be secured to a fastener, such as a paperclip, that is detachably secured to the prescription order.

1. Pharmacy Prescription Order Filling Procedure

Figure 5:
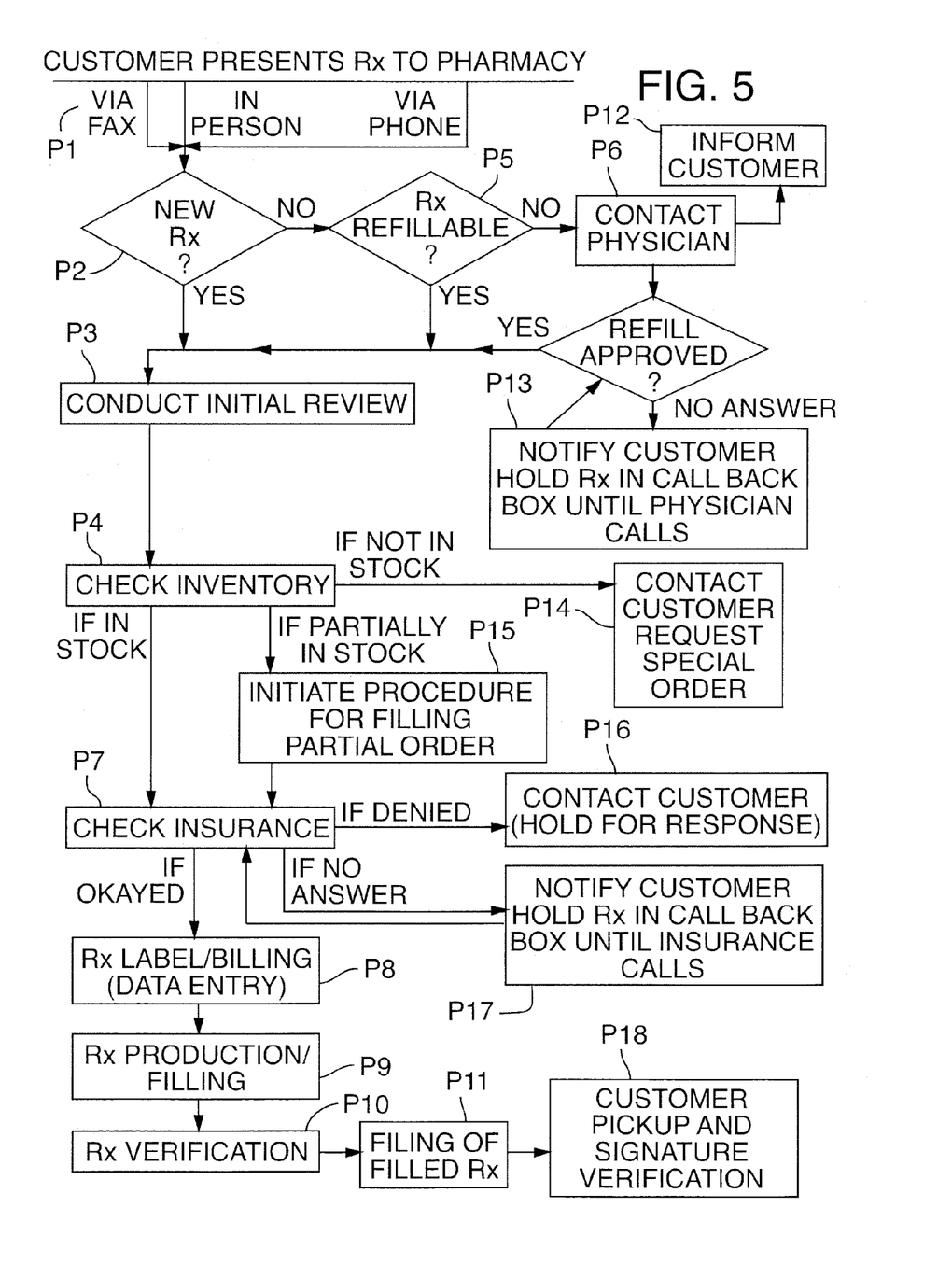
FIG. 5 is a block diagram of an exemplar pharmacy prescription order filling system.

Referring specifically to FIG. 5, an exemplary pharmacy, which is preferably a retail pharmacy, prescription order filling procedure is disclosed. In step P1, a prescription order, which could include a written prescription form, a renewable prescription label, or any other tangible medium documenting a request for a prescription by a health care provider is presented to the pharmacy either in person, via facsimile, via phone, or via a computer transmission, such as e-mail. A pharmacy worker then reviews the prescription order and attaches a unique tag 16 (FIG. 2) to it that is readable by a tag reader 18 (FIG. 4 to determine its location within the pharmacy 14.

As shown in Step P2, the pharmacy worker then determines if the prescription order is for a new prescription. If so, the pharmacy worker conducts an initial review (Step P3) which includes checking the available inventory for the prescribed drug (Step P4), determining if there is available insurance (Step P7) and if required, obtaining approval from the insurer and preparing the label and necessary billing and information disclosure paperwork (Step P8).

If the prescription is not new, the pharmacy worker determines if it is refillable (Step P5). If so, the pharmacy worker then conducts the initial review (Step P3) as previously described. If not, the pharmacy worker contacts the prescribing health care provider (Step P6) to determine if the prescription may be refilled. If the health care provider approves of the refill, the pharmacy worker will then conduct the initial review (Step P3) as previously described. If not, the customer will be informed (Step P12). If the health care provider is not available, the prescription order to placed in a holding area until the health care provider is contacted (Step P13), and the customer is informed of this status.

Regarding Step P4, if the inventory is not in stock, the pharmacy worker typically informs the customer and offers the customer an opportunity to special order the prescribed drug (Step P14). If there is only a partial amount of the prescribed drug in stock, the pharmacy worker will typically initiate a procedure for filling only a partial order (Step P15). This procedure typically includes preparing additional paperwork to alert the customer that only a partial order has been filled, and ordering additional quantities of the prescribed drug.

Regarding Step P7, if the insurance coverage is denied, the prescription order is typically held in an area pending the customer being contacted to request authorization to proceed (Step P16). If the insurer cannot be contacted, the pharmacy has the option to either fill the prescription and alert the customer upon pick-up, or hold the prescription order pending a response from the insurer (Step P17).

After the initial review is complete, the prescription order and related paperwork are presented to a technician for filling (Step P9). The technician fills the prescription order and attaches the label. The technician then presents the filled prescription order and related paperwork to a registered pharmacist for verification (Step P10).

Following verification, the filled prescription is placed in a storage area pending customer pick-up (Step P11). When a customer picks-up the filled prescription, the pharmacy worker complies with applicable customer notice requirements, and obtains the customer's signature (also called "signature capture") confirming that they have received such notice (if applicable) and that they have received the filled prescription (Step P18).

2. Pharmacy Tracking Zones

In practice and referring specifically to FIG. 4, it is more efficient to perform the various steps noted above at spaced apart locations, or zones, throughout the pharmacy. For example, prescription order intake (Step P1 of FIG. 5) and initial review (Step P3 of FIG. 5) can be performed at location 21 (FIG. 4). Label printing and data entry (Step P8 of FIG. 5) could be accomplished at location 27 (FIG. 4). Prescription orders waiting from some form of call back either from the customer, the insurer, or the health care provider could be placed at location 24 (FIG. 4). Orders waiting to be filled could be placed at location 23 (FIG. 4), orders waiting pharmacist review and approval could be place at location 25 (FIG. 4), and approved filled prescription orders could be stored at location 30 (FIG. 4). Obviously, additional zones could be added to accommodate a particular pharmacy's practices and procedures.

Preferably each station includes a tag reader 18 in communication with the computer system 20 for automatically detecting the arrival of the tag 16 attached to the prescription order 12 as it enters each location. More preferably, the tag reader 18 detects both the arrival of the tag 16 in that station, and the departure of that tag 16 from that station, with the time interval at that station being determined and recorded therefrom.

Each tag reader 18 is preferably fixed at a particular location so that detecting the presence of a tag near the device also automatically indicates the location of that tag 16 within the pharmacy. The tag readers 18 can be rigidly mounted to a work area or station, or portable (i.e. handheld) devices that are operably connected to the station so that it can indicate a location within the pharmacy of a detected tag. Such portable devices facilitate scanning of prescription orders that are compiled in bulk, such as container of filled prescriptions where each prescription order in the container has a unique tag 18. Such a bulk container full of prescription order could arrive into the pharmacy from an off-site prescription filling station. In situations where the tag reader can simultaneously detect and record the location of multiple prescription order, a pharmacy worker can wave the tag reader 18 over the container to record the location of all prescription orders in the container.

3. Storage Bin

Space and efficiency can be optimized by storing filled or prescription orders 12 to be held for pick-up into a common storage bin 30. As best shown in FIG. 1, the storage bin 30 includes a plurality of cubbies 32, with each cubby 32 being sized to receive a prescription order 12 and associated filled prescription. Each cubby is uniquely identified 34, such as by being individually numbered, and includes a tag reader 18 of determining whether a particular tag 16 is received within it. Each tag reader 18 is in communication with the computer system 20.

When a prescription order 12 is filled, the prescription order 12 and filled prescription are simply inserted into an available cubby 32. Accordingly, the tag reader 18 associated with that cubby 32 sends a signal to the computer system 20 denoting the particular location and cubby number where the prescription order 12 and filled prescription are held. When a customer arrives to pick-up his or her filled prescription, the worker enters the customer's identifying information into the computer system 20, and the particular bin number of the cubby containing the prescription order 12 and filled prescription or the current location in the filling process is displayed. The worker then locates and removes the filled prescription from the identified cubby and presents it to the customer.

The removal of the prescription order 12 from that particular cubby 32 is detected by the tag reader 18 and reported to the computer system 20. The tag 16 can remain affixed to the prescription order 12 when filed, thereby allowing it to be easily located in the future. Alternatively, the tag 16 may be reused with a new incoming prescription order.

C. Computer System

Those skilled in the art will appreciate that an exemplary embodiment of the present invention relies on and incorporates several common features of modern personal computers. The general use, operation, and construction of a computer system is known and has been disclosed in numerous patents such as U.S. Pat. No. 5,818,447 to Wolf et al. and U.S. Pat. No. 5,752,025 to Shakib et al.

Figure 6:
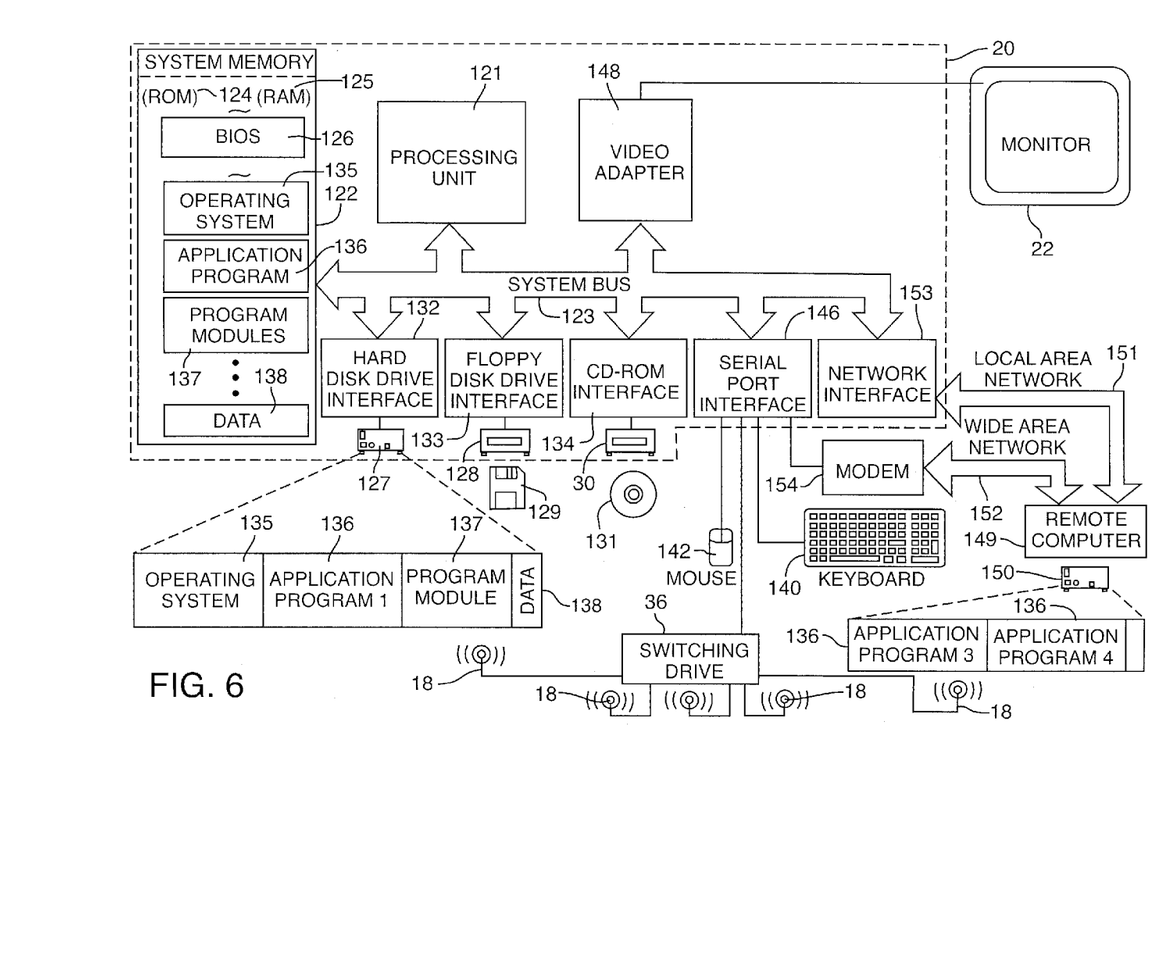
FIG. 6 is a block diagram of an exemplary computer system in accordance with a preferred embodiment of the present invention.

Referring to FIG. 6, the following discussion is intended to provide a brief, general description of a suitable computing environment in which the invention may be implemented. Although not required, the invention will be described in the general context of computer-executable instructions, such as program modules, being executed by a personal computer. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multiprocessor systems, microprocessor-based or programmable consumer electronics, network PCs, minicomputers, mainframe computers, and the like. The invention may also be practiced in distributed computing environments where tasks are performed by remote processing devices that are linked through a communications network. In a distributed computing environment, program modules may be located in both local and remote memory storage devices.

With reference to FIG. 6, an exemplary system for implementing the invention includes a general purpose computer system in the form of a conventional personal computer 20, including a processing unit 121, a system memory 122, and a system bus 123 that couples various system components including the system memory to the processing unit 121. The system bus 123 may be any of several types of bus structures including a memory bus or memory controller, a peripheral bus, and a local bus using any of a variety of bus architectures. The system memory includes read only memory (ROM) 124 and random access memory (RAM) 125. A basic input/output system 126 (BIOS), containing the basic routines that help to transfer information between elements within the personal computer 20, such as during start-up, is stored in ROM 124. The personal computer 20 further includes a hard disk drive 127 for reading from and writing to a hard disk, not shown, a magnetic disk drive 128 for reading from or writing to a removable magnetic disk 129, and an optical disk drive 130 for reading from or writing to a removable optical disk 131 such as a CD ROM or other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of computer readable instructions, data structures, program modules and other data for the personal computer 120. Although the exemplary environment described herein employs a hard disk, a removable magnetic disk 129 and a removable optical disk 131, it should be appreciated by those skilled in the art that other types of computer readable media which can store data that is accessible by a computer, such as magnetic cassettes, flash memory cards, digital video disk, Bernoulli cartridges, random access memories (RAMs), read only memories (ROM), and the like, may also be used in the exemplary operating environment.

A number of program modules may be stored on the hard disk, magnetic disk 129, optical disk 131, ROM 124 or RAM 125, including an operating system 135, one or more application programs 136, other program modules 137, and program data 138. A user may enter commands and information into the personal computer 20 through input devices such as a keyboard 140, pointing device 142, and tag readers 18. Preferably, a plurality of tag readers 18, which are distributed throughout the pharmacy are integrated with a switching device 36 that periodically monitors the status of each tag reader 18 and transmits that information to the personal computer 20. Other input devices (not shown) may include a microphone, joystick, game pad, satellite dish, scanner, or the like.

These and other input devices are often connected to the processing unit 121 through serial port interface 146 that is coupled to the system bus, but may be connected by other interfaces, such as a parallel port, game port or a universal serial bus (USB). A display 22 or other type of display device is also connected to the system bus 123 via an interface, such as a video adapter 148. In addition to the monitor, personal computers typically include other peripheral output devices (not shown), such as speakers and printers.

The personal computer 20 may operate in a networked environment using logical connections to one or more remote computers, such as a remote computer 149. The remote computer 149 may be another personal computer, a server, a router, a network PC, a peer device, a personal digital assistant ("PDA"), or other common network node, and typically includes many or all of the elements described above relative to the personal computer 20, although only a memory storage device 150 has been illustrated in FIG. 7. The logical connections depicted in FIG. 7 include a local area network (LAN) 151 and a wide area network (WAN) 152. Such networking environments are commonplace in offices, enterprise-wide computer networks, intranets and the Internet.

When used in a LAN networking environment, the personal computer 20 is connected to the local network 151 through a network interface or adapter 153. When used in a WAN networking environment, the personal computer 20 typically includes a modem 154 or other means for establishing communications over the wide area network 152, such as the Internet. The modem 154, which may be internal or external, is connected to the system bus 123 via the serial port interface 146. In a networked environment, program modules depicted relative to the personal computer 20, or portions thereof, may be stored in the remote memory storage device. It will be appreciated that the network connections shown are exemplary and other means of establishing a communications link between the computers may be used.

Preferably, a plurality of networked personal computers 20 are positioned within the pharmacy, one at the intake area (21, FIG. 4), one at the customer pick-up area (29, FIG. 4), and one at the data entry/label area (27, FIG. 4).

D. Exemplar Application Program

In addition to tracking prescription orders through the system, the information gathered by the computer system can also be used to identify particular prescription orders within the pharmacy that need special attention by the pharmacy workers and activate one or more transducers on the tags associated with those particular prescription orders.

Figure 7:
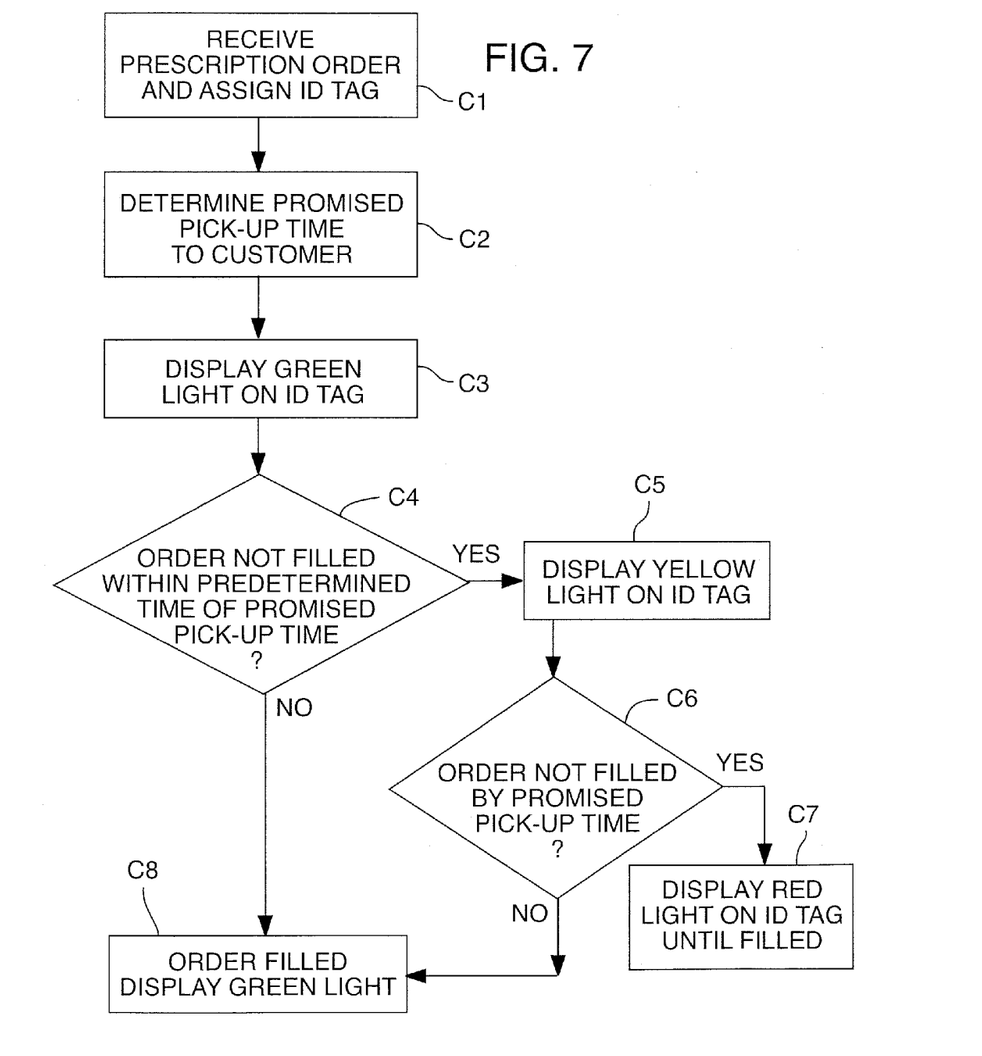
FIG. 7 is a block diagram of an exemplary application program in accordance with a preferred embodiment of the present invention.

For example, the tracking system can be used to identify and alert pharmacy workers that a particularly prescription order is at risk of falling behind schedule or actually fallen behind schedule. A block diagram of an exemplar application performing this function is shown in FIG. 7.

The detailed description which follows is represented largely in terms of processes and symbolic representations of operations by conventional computer components, including a processing unit, memory storage devices for the processing unit, and a display device. These operations include the manipulation of data bits by the processing unit and the maintenance of these bits within data structures resident in one or more of the memory storage devices. Such data structures impose a physical organization upon the collection of data bits stored within memory and represent specific electrical or magnetic elements. These symbolic representations are the means used by those skilled in the art of computer programming and the construction of computing devices to most effectively convey teachings and discoveries to others skilled in the art.

For purposes of this discussion, a process is generally a sequence of steps executed by a computing device leading to a desired result. These steps generally require physical manipulations of physical quantities. Usually, although not necessarily, these quantities take the form of electrical, magnetic, or optical signals capable of being stored, transferred, combined, compared, or otherwise manipulated. It is conventional for those skilled in the art to refer to these signals as bits, values, elements, symbols, characters, terms, numbers, records, files or the like. It should be kept in mind however, that these and similar terms should be associated with appropriate physical quantities for computing device operations, and that these terms are merely conventional labels applied to physical quantities that exist within and during operation of the computing device.

It should also be understood that manipulations within the computing device are often referred to in terms such as adding, comparing, moving, etc. which are often associated with manual operations performed by a human operator. The operations described herein are machine operations performed in conjunction with a human operator or user that interacts with a control device. The machines used for performing the operation of the preferred embodiment of the present invention, as will be understood, include a control device and other suitable input devices.

In general, in step C1, the computer system 20 initially associates a particular customer with a tag, which has been attached to the prescription order. Preferably, customer name and other identifying information is associated with that tag at this time and stored in memory.

In step C2, the pharmacy worker or the computer system, determines a predetermined promised pick-up time, that is associated with the prescription order and stored in memory.

In step C3, the computer system activates a first transducer, such as a green light, on the tag associated with the customer order, that transducer is known by the pharmacy worker to denote the prescription order is on schedule.

Step C4 shows that if within a predetermined time of the promised pick-up time the order has not yet been filled, the computer system turns off the first transducer (green light) and activates a second transducer, such as a yellow light, on the tag associated with the customer's prescription order (Step C5). The second transducer is known by the pharmacy worker to denote the prescription order is behind schedule and should be given priority.

In step C6, if the prescription order is not filled by the promised pick-up time, the computer system turns off the second transducer (yellow light), and commands a third transducer, such as a red light, on the tag associated with the customer's prescription order (step C7). The third transducer is known by the pharmacy worker to denote that the prescription order has missed its promised pick-up time and should be given the highest priority. Otherwise, turn on the first transducer when the order is complete (step C8).

In view of the wide variety of embodiments to which the principles of the invention can be applied, it should be apparent that the detailed embodiments are illustrative only and should not be taken as limiting the scope of the invention. Rather, the claimed invention includes all such modifications as may come within the scope of the following claims and equivalents thereto.

What is claimed is:

1. A method for identifying a prescription order in a pharmacy including the following steps:
   receiving the prescription order;
   tagging the prescription order with a wireless tag that travels with the prescription order thorough the pharmacy, said tag having a worker signaling device operably secured thereto and in communication with a central pharmacy computer system, said computer system correlating said prescription order with said tag;
   establishing a timing element in communication with said computer system, said timing element timing an event related to a status of said prescription order and used by the computer system to detect a predetermined criteria of said status; and,
   activating the worker signaling device to alert a pharmacy worker when said predetermined criteria is detected by said computer system.

2. The method for identifying a prescription order in a pharmacy of claim 1, wherein said tagging the prescription order with a wireless tag step includes the tag having a plurality of worker signaling devices operably secured thereto, each device being activated to alert a pharmacy worker to a different status of the prescription order.

3. The method for identifying a prescription order in a pharmacy of claim 1, wherein said worker signaling device is a transducer operably secured to the tag.

4. The method for identifying a prescription order in a pharmacy of claim 3, wherein said transducer is a light.

5. The method for identifying a prescription order in a pharmacy of claim 3, wherein said transducer is an audio speaker.

6. The method for identifying a prescription order in a pharmacy of claim 3, further including a plurality of transducers, and wherein each transducer of the plurality of transducers is independently operable to denote a different status of the prescription order.

7. The method for identifying a prescription order in a pharmacy of claim 6, wherein said plurality of transducers includes lights and at least one audio-speaker.

8. The method for identifying a prescription order in a pharmacy of claim 6, wherein said plurality of transducers includes a plurality of lights, each light having a different color.

9. The method for identifying a prescription order in a pharmacy of claim 1, wherein said activating the worker signaling device step includes wirelessly transmitting a command signal from a transmitter operably secured to the computer system to a receiver operably secured to the tag.

10. The method for identifying a prescription order in a pharmacy of claim 1, wherein said activating the worker signaling device step includes wirelessly transmitting a command signal from a tag reader operably secured to a computer system to a receiver operably secured to the tag, and further including the step of:
    automatically tracking said tag in the pharmacy based on the proximity of the tag to the tag reader.

11. The method for identifying a prescription order in a pharmacy of claim 10, wherein said tag is an RFID tag with a transducer operably secured thereto.

12. The method for identifying a prescription order in a pharmacy of claim 10, wherein further including the step of:
    displaying the location of the tag on a computer display of the computer system.

13. The method for identifying a prescription order in a pharmacy of claim 1,
    wherein said predetermined criteria includes using the timing element to determine how long said prescription order has remained at a defined location within said pharmacy.

14. The method for identifying a prescription order in a pharmacy of claim 1, wherein said timing element includes a timer internal to the tag.

15. The method for identifying a prescription order in a pharmacy of claim 1, wherein said timing element resides in a computer system that is wirelessly connected to the tag.

16. The method for identifying a prescription order in a pharmacy of claim 1, wherein said activating the worker signaling device to alert a pharmacy worker step is initiated by a pharmacy worker using a computer system wirelessly connected to the tag.

17. The method for identifying a prescription order in a pharmacy of claim 1, wherein said activating the worker signaling device to alert a pharmacy worker step is automatically initiated by a computer system wirelessly connected to the tag in response to a predefined criteria.

* * * * *